United States Patent [19]

Evans, III et al.

[11] Patent Number: 4,854,330
[45] Date of Patent: Aug. 8, 1989

[54] FORMED CORE CATHETER GUIDE WIRE ASSEMBLY

[75] Inventors: Russell M. Evans, III, Lower Burrell; James E. Machek, Valencia; Kevin P. Cowan, Allison Park, all of Pa.

[73] Assignee: Medrad, Inc., Pittsburgh, Pa.

[21] Appl. No.: 244,610

[22] Filed: Sep. 9, 1988

Related U.S. Application Data

[63] Continuation of Ser. No. 883,943, Jul. 10, 1986, abandoned.

[51] Int. Cl.$^4$ .............................................. A61B 5/00
[52] U.S. Cl. ..................................... 128/772; 604/264
[58] Field of Search .......................... 128/656–658, 128/772; 604/95, 158, 164, 166, 170, 171, 264

[56] References Cited

U.S. PATENT DOCUMENTS

| | | | |
|---|---|---|---|
| 2,865,374 | 12/1958 | Brown et al. | 604/171 |
| 3,452,742 | 7/1969 | Muller | 128/772 |
| 4,003,369 | 1/1977 | Heilman et al. | |
| 4,215,703 | 8/1980 | Willson | 128/772 |
| 4,402,684 | 9/1983 | Jessup | 604/264 |
| 4,498,482 | 2/1985 | Williams | 128/786 |
| 4,538,622 | 9/1985 | Samson et al. | 128/772 |
| 4,545,390 | 10/1985 | Leary | 604/95 |
| 4,548,206 | 10/1985 | Osborne . | |
| 4,619,274 | 10/1986 | Morrison | 604/170 |
| 4,676,249 | 6/1987 | Arenas et al. | 604/170 |
| 4,684,369 | 8/1987 | Wildemeersch | 604/264 |

FOREIGN PATENT DOCUMENTS

| | | | |
|---|---|---|---|
| 0976993 | 11/1982 | U.S.S.R. | 604/158 |
| 1435797 | 5/1976 | United Kingdom | 128/657 |

OTHER PUBLICATIONS

USCI, Safety Spring Guides–Stainless Steel & Teflon Coated, 1974.

Primary Examiner—Max Hindenburg
Attorney, Agent, or Firm—Fleit, Jacobson, Cohn, Price, Holman & Stern

[57] ABSTRACT

A core wire insertable in a catheter guide wire assembly provides a defined degree of rigidity to the catheter assembly to allow the assembly to be maneuvered through the tortuous path of the vascular or other system of a patient. The core wire includes, at its distal end, a paddle having a substantially barrel-shaped body, leading to a continuous chamfer which terminates in a truncated end. Further, the core wire can have a curved section adjacent its distal end. The curved section is made by press hardening the generally circular core wire into a substantially rectangular shape such that the press hardened wire memorizes the arc of curvature. When the core wire is press hardened into a rectangular shape, a singular degree of freedom of movement is imparted to the wire in contrast to the two degrees of freedom of movement of the cross-sectionally circular core wire. A method of manufacture is also described using concave/convex mating dies or flat plate dies.

11 Claims, 3 Drawing Sheets

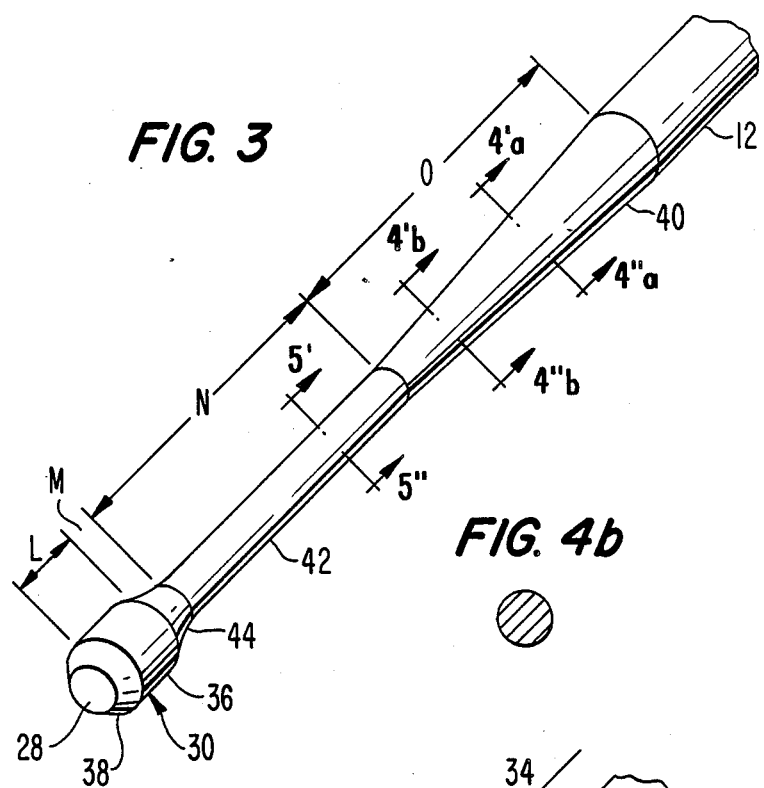
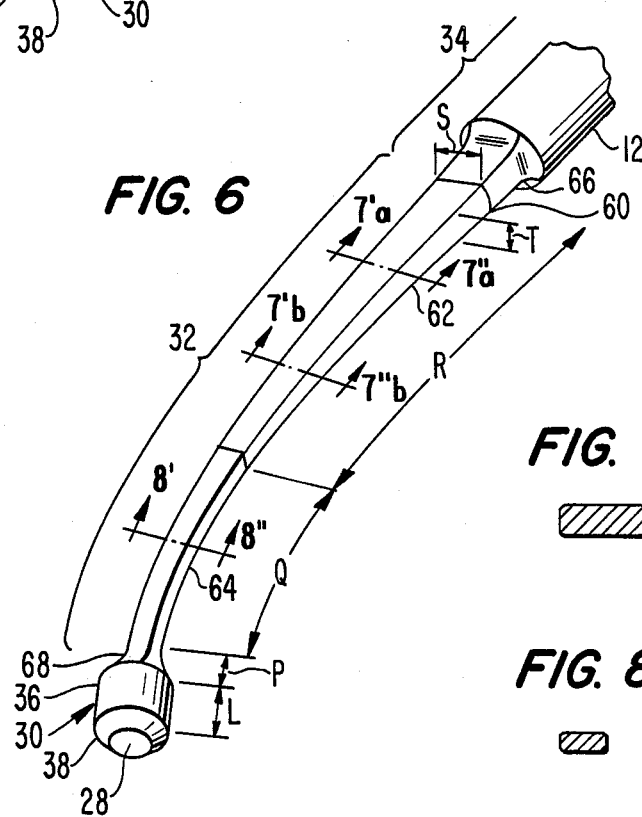
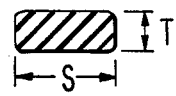

FORMED CORE CATHETER GUIDE WIRE ASSEMBLY

This application is a continuation of application Ser. No. 883,943, filed July 10, 1986, now abandoned.

BACKGROUND OF THE INVENTION

This invention relates to a catheter guide wire assembly and particularly relates to a core wire insertable in the assembly and to a distal tip configuration for that core wire.

In medical procedures such as angiography, a catheter must be positioned deep in the vascular system, and often such catheters must reach difficult to access regions. In order to introduce such a catheter into the vascular system of a patient, a sharp cannula is inserted through the skin and into the vascular system, and then a spring guide wire is inserted through the cannula. The cannula is then removed from the patient's body and the catheter is inserted into the body by sliding over the guide wire. The guide wire generally then is withdrawn, and the catheter is ready for further positioning and use. Catheters are also used in non-vascular procedures such as urinary tract procedures, and are introduced, as described above, with the aid of the catheter guide wire.

As used herein, the terms "catheter" and "guide wire" are meant to encompass all types of catheters and guide wires. For convenience, however, the specific example discussed herein relates to procedures dealing with the vascular system. The present invention is not limited to catheters and guide wires designed for the vascular system, and hence the benefits and advantages of the present invention apply equally to any medical procedure where a catheter must be feed through the skin and reach a remote location in the human body.

As stated earlier, the catheter guide wire assembly is inserted into the vascular system prior to the insertion of the catheter over the guide wire. The guide wire must be flexible and yet strong enough to negotiate the desired tortuous path of the vascular system and yet do no damage with its leading tip. Further, the guide wire must be strong enough to resist doubling back, kinking or breaking during the insertion and retraction processes.

Some catheter guide wire assemblies are one piece guide wire assemblies which include a wound outer casing with an ultra smooth surface and a safety core wire extending longitudinally within the casing and attached to each end thereof. This type of catheter guide wire assembly is described more fully in U.S. Pat. No. 4,003,369 by Heilman et al, the disclosure of which is incorporated herein by reference thereto. The core wire of the catheter guide wire assembly provides a degree of strength for the outer casing and appropriate rigidity such that the entire assembly can negotiate the vascular system. The flexibility of the entire guide wire assembly can be altered by changing the flexibility of the core wire at different longitudinal sections along the length thereof. In the Heilman et al patent discussed above, the core wire is tapered in a region proximate to its distal end to enhance its flexibility.

Due to the tortuous path the catheter guide wire assembly must take in the vascular system, and due to the need for selective rigidity and flexibility in the guide wire, a guide wire has been developed with a core wire insertable and movable within the catheter guide wire assembly. With an insertable core wire, the flexibility of the guide wire assembly at the tip can be altered by moving the core wire into and out of the region adjacent the distal end. Still, a great deal of skill is needed to guide the wire into the desired location in the vascular system, and to do so without damaging the vascular system itself. Also, with such a catheter guide wire assembly, care must be taken to minimize the possibility of the distal end of the core wire punching through the wound outer casing of the guide wire at the distal end thereof and also at other locations along the length of the guide wire assembly.

OBJECTS OF THE INVENTION

It is an object of the present invention to provide a catheter guide wire assembly whose flexibility depends upon the flexibility of an insertable formed core wire.

It is another object of the present invention to minimize the possibility of the insertable core wire punching through the wound outer casing of the catheter guide wire assembly.

It is an additional object of the present invention to provide a catheter guide wire assembly having an insertable core wire with a curve in the region adjacent the distal end thereof.

It is another object of the present invention to provide a catheter guide wire assembly which is capable of one degree of movement rather than two degrees due to the shape of the insertable formed core wire.

SUMMARY OF INVENTION

A core wire insertable in a catheter guide wire assembly provides a defined degree of rigidity to the catheter assembly to allow the assembly to be maneuvered through the tortuous path of the vascular or other system of a patient. The core wire includes, at its distal end, a paddle having a substantially barrel-shaped body, leading to a continuous chamfer which terminates in a truncated end. Further, the core wire has a curved section adjacent its distal end. The curved section is made by press hardening the generally circular core wire into a substantially rectangular shape such that the press hardened wire memorizes the arc of curvature. When the core wire is press hardened into a rectangular shape, a singular degree of freedom of movement is imparted to the wire in contrast to the two degrees of freedom of movement of the cross-sectionally circular core wire. The method of manufacture involves constraining the designated section of wire in a concave or over a mating convex die and press hardening the wire. Another method is constraining the wire in a curve and press hardening the wire between two flat dies.

BRIEF DESCRIPTION OF THE DRAWINGS

The invention, together with further objects and advantages thereof, may best be understood by reference to the following description taken in conjunction with the accompanying drawings in which:

FIG. 3 illustrates the distal end and the adjacent intermediate region of the core wire in accordance with an embodiment of the invention;

FIGS. 4a, 4b and 5 are cross-sectional views from the perspective of section lines 4a'–4a"; 4b'–4b" and 5'-5" in FIG. 3;

FIG. 6 illustrates a curved core wire in accordance with another embodiment of the present invention;

FIGS. 7a, 7b and 8 are cross-sectional views from the perspective of section lines 7a'–7a"; 7b'—7b' and 8'—8' in FIG. 6;

DETAILED DESCRIPTION

The present invention relates to a catheter guide wire assembly and particularly relates to a core wire which is insertable in the guide wire assembly.

Figure 1:
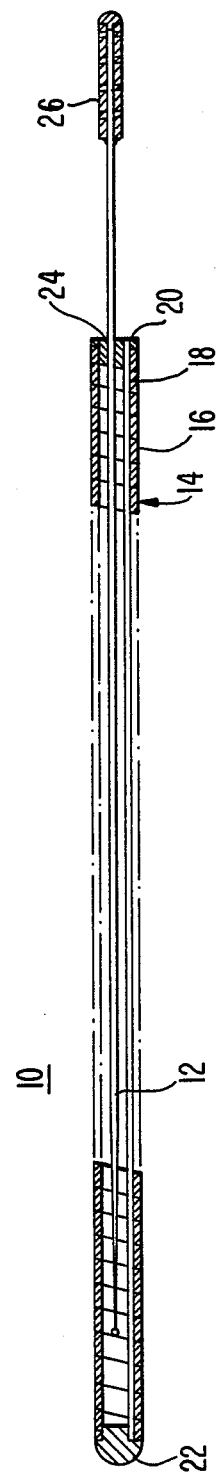
FIG. 1 illustrates a catheter guide wire assembly with a partially withdrawn, insertable core wire in accordance with an embodiment of the present invention.

FIG. 1 illustrates a partial, longitudinal cross-sectional view of a catheter guide wire assembly 10 in accordance with one embodiment of the present invention. Particularly, the catheter guide wire assembly 10 includes an insertable core wire 12 partially inserted into a casing assembly 14.

An example of casing assembly 14 includes a wound outer casing 16 and could include a safety wire 18 affixed to the proximal end 20 of assembly 14 and the distal end 22 of that assembly. The wound outer casing takes the form of a coiled spring which is developed from a wound wire, such as flat wire. The outer surface of casing 16 can be an ultra smooth surface developed by coating the base flat wire with a lubricating agent such as teflon prior to being spring-wound. In this manner, flaking of the outer coating is minimized during bending of the guide wire when in use. Also, the surface of the casing can be lightly ground by abrasion and subsequently electro-polished. Safety wire 18 is welded, or is affixed in some other fashion, to proximal end 20 and distal end 22 of wound outer casing 16. A further description of a specific casing assembly can be found in U.S. Pat. No. 4,003,369 by Heilman et al, assigned to the assignee of the present invention, and that description is incorporated herein by reference thereto.

The casing and safety wire assembly 14 is relatively flexible; therefore, core wire 12 is adapted to be inserted into open end 24 at proximal end 20 of casing and safety wire assembly 14. Core wire 12 is illustrated as being partially inserted in catheter assembly 10 in FIG. 1. When fully inserted into casing and safety wire assembly 14, core wire 12 provides a degree of rigidity such that the entire catheter guide wire assembly 10 can negotiate the tortuous path through the vascular system, or other system, of the patient. The degree of rigidity of catheter assembly 10 is primarily dependent upon the rigidity or flexibility of core wire 12.

Core wire 12 includes at its proximal end a wound handle 26 such that the medical personnel can insert and withdraw core wire 12 from casing and safety wire assembly 14.

Figure 2:
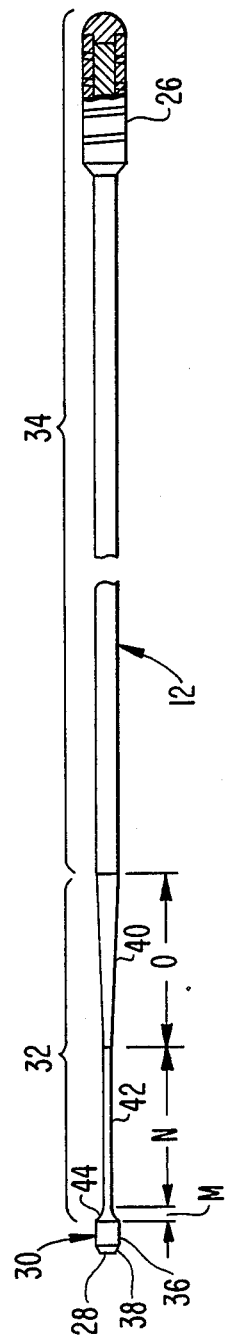
FIG. 2 illustrates the insertable core wire in accordance with an embodiment of the invention.

FIG. 2 illustrates a partial longitudinal view of core wire 12 with handle 26 showing a partial breakaway cross-sectional view thereof. In general, core wire 12 is an elongated, resilient metal core wire having a distal end 28 at which is formed a paddle 30, an intermediate region 32 and a proximal region 34. The total length of core wire 12 is such that a portion of the proximal region extends beyond proximal end 20 (see FIG. 1) of casing and safety wire assembly 14.

Paddle 30 has a substantially barrel-shaped body 36 which in one embodiment has a cross-sectional area substantially equal to the cross-sectional area of core wire 12 in the proximal region 34. Paddle 30 also includes a continuous chamfer 38 extending to the truncated distal end 28 of core wire 12. The truncated end is substantially flat and at a right angle with respect to the longitudinal axis of core wire 12. Paddle 30 can generally be called "a bullet nose." Chamfer 38 is continuous in that it extends around the circumference of barrel-shaped body 36. One method of forming chamfer 38 is to grind the end of body 36 on a centerless grinder. Another method is to dip body 36 into phosphoric acid and pass an electric current therethrough. The electro-etching concentrates on the sharp edge of barrel-shaped body 36 and therefore etches the edge away. By timing the electro-chemical etching, chamfer 38 is formed on body 36. In this situation, chamfer 38 may be slightly bowed rather than a straight inclined plane extending from the circumference of barrel-shaped body 36 to truncated distal end 28 f the core wire. Experimental tests have shown that the "bullet nose" paddle reduces the possibility of punch through.

Intermediate region 32 is generally defined by a first part 40, a second part 42 and a tapered section 44. The first part 40 has a circular cross-sectional area which is longitudinally attenuated from proximal region 34 to the second part 42, over a distance 0. The second part 42 has a cross-sectional area which is substantially uniform throughout its longitudinal length N. Taper 44, spanning distance M is a uniform taper to the larger diameter barrel-shaped body 36 of paddle 30. In one embodiment, the cross-sectional area of the proximal region 34 is substantially uniform throughout its length. Therefore, core wire 12 imparts the greatest rigidity to catheter assembly 10 throughout proximal region 34 and imparts a lesser degree of rigidity, i.e., greater flexibility, to the catheter assembly throughout its intermediate region 32. By increasing length 0 of longitudinal attenuated part 40, the core wire would impart greater degrees of flexibility to the catheter assembly. In a similar fashion, the present invention can be embodied by providing a plurality of longitudinally attenuated parts 40, each having different degrees of taper. In this alternative embodiment, the flexibility of the core wire and hence the catheter assembly would be further enhanced. The present invention is meant to encompass a plurality of longitudinally attenuated cross-sectional areas.

Parts 40 and 42 of intermediate region 32 are formed by placing a core wire 12, which can be a high grade stainless steel, 300 series work hardenable, between a specially configured grinding wheel and a regulation wheel. At that time, taper 44, uniform part 42, and longitudinally attenuated part 40 are formed by centerless grinding of the integral core wire.

FIG. 2 illustrates handle 26 at the proximal end of core wire 12. Handle 26 is only exemplary of a plurality of handles which can be placed at the end of core wire 12 to enable the medical personnel to insert and withdraw the core wire from the catheter assembly. In the illustrated embodiment, handle 26 comprises a plurality of wound flat wire coils which are welded at either end to the core wire.

In one embodiment, proximal region 34 of core wire 12 can have a diameter from 0.010 to 0.022 of 304 stainless steel. Length O is three inches, length N is one inch and the diameter of uniform part 42 is 0.007 inches. The diameter of barrel-shaped body 36 of paddle 30 is in the same range as the diameter of the core wire in proximal region 34.

FIG. 3 illustrates a perspective view of core wire 12 at the intermediate region 32 and the distal end section of the core wire. FIGS. 4a, 4b and 5 show cross-sectional areas of longitudinally attenuated part 40 and uniform part 42.

The core wire described in conjunction with FIGS. 2 and 3 has substantially two degrees of freedom of movement. To explain, if the core wire were mounted along the Z axis in a hypothetical three plane cartesian coordinate system with the Z axis extending perpendicularly through an XY plane, the distal end of the core wire could move in an unrestricted fashion in the X direction, in the Y direction and a combination of those two. Since the wire is constrained along the Z axis, the wire would not move along the Z direction. In this sense, the core wire has two degrees of freedom of movement, in the X and Y direction.

In another embodiment of the present invention, illustrated in FIG. 6, a formed core wire has substantially only one degree of freedom of movement. FIG. 6 generally shows the intermediate region in the distal end of core wire 12. In addition, a limited section of proximal region of 34 is illustrated at the top of FIG. 6. In general, core wire 12 has a continuously curved section adjacent distal end 28, when the core wire is in its relaxed state. The curved section is defined by intermediate region 32, however, the curved section need not be so limited and may be only a portion of the intermediate region rather than the entire intermediate region.

The curved section of core wire 12 is formed by placing the wire portions to be curved in a concave die and press hardening or coining the constrained wire with a mating convex die. In this manner, the cross-sectional area of the curved section is press hardened into a substantially rectangular shape. As used herein, the term "rectangular shape" means a shape which conforms grossly to FIG. 7a, i.e., a shape having at least two substantially parallel sides to provide preferential flexibility in one plane. By press hardening in a concave die, the major axis S in FIGS. 6 and 7a of the rectangular shape is normal to the plane defined by the curvature of the curved section. Conceptually, the curved section lies in a plane and that plane is called herein "the plane of curvature." The major axis of the rectangular shape is the lengthwise aspect thereof. When the wire is press hardened in concave/convex mating dies, the major axis is normal to the plane of curvature and the minor axis, or the widthwise aspect, of the rectangular shape is aligned parallel to the plane of curvature. Another method of forming a curved section of the core wire is to constrain the appropriate section of wire in a curve on a flat die and to press harden or coin the constrained wire with a mating flat die. In this manner, a substantially rectangular cross-sectional wire is obtained and the minor axis T of the rectangular shape is normal to the plane of curvature of the core wire. With this embodiment, the lengthwise aspect (the major axis S) of the rectangular shape is parallelly aligned to the plane of curvature of the wire location.

Returning to FIG. 6, the proximal region 34 ends at 60. The first part 62 of intermediate region 32 has a longitudinally attenuated cross-sectional area (compare FIGS. 7a and 7b) over length R, and the second part 64 has a substantially uniform cross-sectional area throughout its length Q. The longitudinally attenuated cross-sectional areas of the intermediate region are shown in FIGS. 7a, 7b and FIG. 8 along the appropriate section lines illustrated in FIG. 6.

To reduce the stress concentration between the more proximal portion of core wire 12 and the rectangularly-shaped intermediate region 32, a transitional slope 66 is provided between the flattened and curved section of the wire and the circular section of the wire. Also, a second transitional slope 68 is provided between the second part 64 of intermediate region 32 and paddle 30. Paddle 30 is not curved and, therefore, the longitudinal length L of barrel-shaped body 36 is substantially the same as that noted above with respect to the core discussed in conjunction with FIG. 3.

Figure 9:
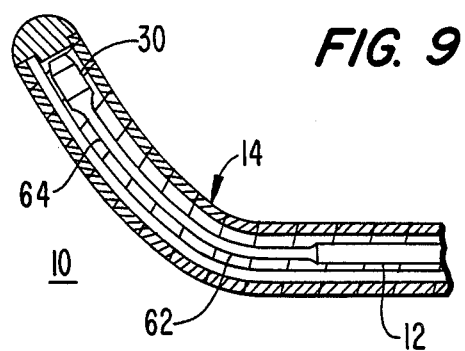
FIG. 9 illustrates a portion of the curved core wire in accordance with an embodiment of the present invention; and, FIGS. 10a, 10b, 11a and 11b illustrate a curved core wire, each having one degree of freedom of movement but in different planes with respect to the plane of the curve, as other embodiments in accordance with the principles of the present invention.

The stainless steel chosen for core wire 12 is such that it is work hardenable and, therefore, when the wire is constrained in a curve and coined, the wire will retain the curve or memorize the curve. However, the curved section of the core wire still is flexible, that is, the curved section is not rigid to all movement. By providing a curved section in the core wire, the medical personnel can advance or retract this core and hence the distal end of the catheter assembly becomes either very floppy, by withdrawing the core, or stiffer by advancing the core. Further, when the curved section of the core is fully inserted into the distal end of the catheter assembly, as shown in FIG. 9, the catheter assembly follows the curved section and takes on a curved shape such that the medical personnel can enter a selected artery by directing the core wire appropriately. Further, the core wire is torqueable, and hence the curved tip of the guide wire can be steered by turning the handle 26 of the core wire. It is contemplated that arcs of two, three and six inches can be embodied by the curved section of the core wire. Hence, different core wires can have different degrees of arc.

It is known to utilize a guide wire with a "J" tip at the distal thereof. These "J" tipped configurations range in size from 1 mm to as large as 15 mm. Their main function is to reduce trauma to the arterial system as they negotiate torturous curvatures in the vessel, thereby reducing the propensity for perforating the vessel. Usually it is standard practice for this "J" tipped guide wire to extend beyond the catheter in order for the guide wire to find its way with the "bottom" of the "J" and then the catheter to be advanced upon the correct section of the artery having been steered by the guide wire. The "J" shape in the guide wire is considered by some to be a safer configuration. Also, various shapes can be placed at the distal portion of catheters, which perform quite a different function. The unique shape of the distal portions of the catheter is used to selectively determine the vessel which requires entry.

Therefore, the "J" shape of the guide wire is mainly for the purpose of minimizing trauma as it negotiates a vessel. There is no relationship to the above-described "J" shape and the arc that is placed in the formed core of the present invention. This arc or radius at the distal portion of the guide wire is for the purpose of steering or selecting a vessel at a branch or bifurcation in a vessel. The distal tip of the formed core is precisely steered through the vascular system whereas only the "bottom" of the "J" is at the forefront of the "J" tipped guide wire, i.e., the distal end of that core wire is not the most distal portion of the entire guide wire. The degree of arc of the present invention is something less than the arc in "J" tipped guide wires and, in preferred embodiments, not greater than 90 degrees.

FIG. 9 illustrates a partial cross-sectional longitudinal view of catheter assembly 10 with the curved section, which includes parts 62 and 64 of the intermediate region, and with core wire 12 fully inserted within casing and safety wire assembly 14. As shown, the catheter assembly 10 has a curved aspect which follows the curved core wire.

FIGS. 10a, 10b, 11a and 11b show front and side views of curved, flattened core wires having substantially one degree of freedom of movement.

Figure 10A:
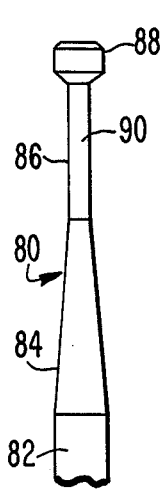
Figure 10B:
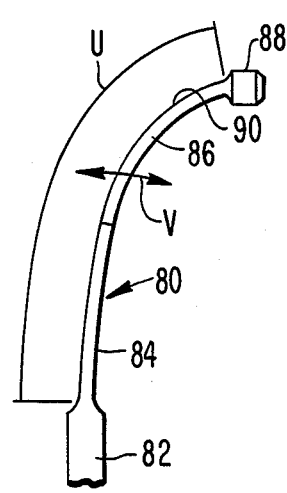

FIGS. 10a and 10b show front and side views of a curved core wire 80. Proximal region 82 leads to longitudinally attenuated section 84 which in turn leads to uniform section 86 and ultimately to paddle 88 at the distal end of core wire 80. FIG. 10b shows the side view of core wire 80. The plane of curvature is the surface of the drawing sheet in FIG. 10b. The major axis of the rectangularly-shaped section of the wire, illustrated generally by surface 90, follows curvature U which in turn generally describes the curvature of core wire 80 in the plane of curvature. The surface 90, generally aligned with the major axis, is normal to the plane of curvature. In this case, core wire 80 has a substantially singular degree of freedom of movement illustrated by double arrowed line V.

To explain, returning to the theoretical positioning of core wire 80 along the Z axis in a three-dimensional cartesian coordinate system, if the major axis (generally surface 90) of the rectangular cross-sectionally-shaped core wire 70 is parallel to the Y axis, the core wire exhibits substantially a singular degree of freedom of movement in the X direction or along the X axis (e.g., see arrow V). It is to be understood that flattening the core wire does not limit all movement along the Y axis, but movement along the Y axis is substantially diminished as compared with movement along the X axis due to the comparative lengths along the major and minor axes of the body (compare surface 90 to surface 86). Therefore, the single degree of freedom of movement discussed with respect to the present invention means that preferential bending or flexing in one direction is introduced by the flattening or press hardening of the core wire.

Figure 11A:
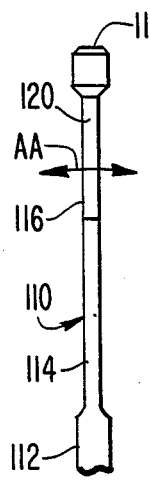
Figure 11B:
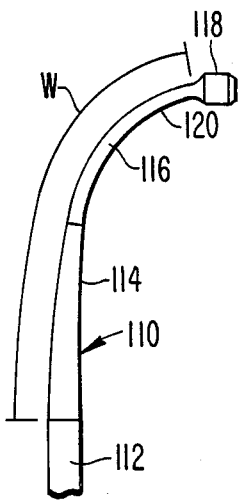

In FIGS. 11a and 11b, the front and side views of a curved core wire 110 are illustrated. Core wire 110 includes proximal region 112, an intermediate region including longitudinally attenuated section 114, and uniform section 116, and paddle 118 at the distal end of the core wire. As illustrated in FIG. 12b, the minor axis of the rectangularly-shaped core wire sections, generally along surface 120, follows the arc of curvature of arc W such that core wire 110 exhibits a singular degree of freedom of movement as shown by double arrowed line AA in FIG. 11a. Surface 120 is normal to the plane of curvature and surface 116 is parallelly aligned to that plane.

While only certain preferred features of the invention have been shown by way of illustration, many modifications and changes can be made. It is to be understood that the appended claims are intended to cover all such modification and changes as fall within the true spirit and scope of the invention.

What we claim is:

1. A formed core catheter guide wire assembly comprising:
    a smooth surfaced wound wire casing having a closed end and an open end, and
    an elongated, resilient metal core wire having a distal end and a proximal region, with a portion of said proximal region extending beyond said open end of said casing, said core wire being slidably mounted in said casing and having a preformed, continuously curved section adjacent said distal end, said preformed, continuously curved section being flexible and said preformed, continuously curved section maintaining a curved configuration when in a relaxed state for steering of the guide wire assembly through the vascular system of the body,
    said preformed, continuously curved section having a first part that has a longitudinally attenuated, generally rectangular cross-sectional area and a second part having a substantially uniform, generally rectangular cross-sectional area extending from said first part to said distal end, said proximal region having a substantially circular cross-sectional area, and said core wire including a continuously curved first transitional slope between the circular proximal region and the rectangular first part of said curved section and including a continuously curved second transitional slope between the uniform rectangular second part of said curved section and said distal end.

2. A formed core catheter assembly as claimed in claim 1 wherein the major axis of all the rectangularly cross-sectional portions of said core wire is normal to the plane of curvature of said curved section.

3. A formed core catheter assembly as claimed in claim 1 wherein the minor axis of all the rectangularly cross-sectional portions of said core wire is normal to the plane of curvature of said curved section.

4. A formed core catheter assembly as claimed in claim 1 wherein the arc of curvature of said curved section is not greater than 90 degrees.

5. A formed core catheter assembly as claimed in claim 1 wherein said distal end includes a paddle having a substantially circular cross-sectional area which terminates in a continuous chamfer at a truncated end of said core wire.

6. A formed core catheter guide wire assembly comprising:
    a smooth surface wound wire outer casing having an open end, and
    an elongated, resilient metal core wire having a distal end and a proximal region, with a portion of said proximal region extending beyond said open end of said casing, said distal end having a barrel-shaped body and a continuous chamfer extending to a truncated end of said core wire, said core wire being slidably mounted in said casing and having a preformed, continuously curved section adjacent said distal end, said preformed continuously curved section being flexible and said preformed, continuously curved section maintaining a curved configuration when in a relaxed state for steering of the guide wire assembly through the vascular system of the body.

7. A catheter guide wire assembly as claimed in claim 6 wherein said chamfer extends around the circumference of said barrel-shaped body.

8. A formed core catheter guide wire assembly comprising:

an elongated outer casing defined by an elongated rectangular flat wire wound into a coil spring, the surface of said outer casing being defined by the radially outer surface of consecutive contacting coils, and an insertable and movable core wire which is an elongated resilient metal core wire having a distal end that includes a barrel-shaped body and a continuous chamfer extending to a truncated end of said core wire, said core wire being slidably mounted in said casing and having a preformed, continuously curved section adjacent said distal end, said preformed, continuously curved section being flexible and said preformed, continuously curved section maintaining a curved configuration when in a relaxed state for steering of the guide wire assembly through the vascular system of the body.

9. A catheter guide wire assembly as claimed in claim 8 wherein said outer casing is closed at one end and open at the other end and includes a safety wire extending longitudinally within said outer casing and is attached to the ends thereof, said core wire includes a proximal region which extends beyond said open end of said assembly when said core wire is fully inserted within said casing.

10. A catheter guide wire assembly as claimed in claim 9 wherein said chamfer at said distal end extends around the circumference of said barrel-shaped body.

11. A formed catheter guide wire assembly comprising:

a smooth surfaced wound wire casing having a closed end and an open end, and an elongated, resilient metal core wire having a distal end and a proximal region, with a portion of said proximal region extending beyond said open end of said casing, said proximal region having a circular cross-sectional shape and said core wire being slidably mounted in said casing and extendable to said closed end of said casing to guide said casing and said core wire having a preformed, continuously curved section located adjacent said distal end, said preformed, continuously curved section having a generally rectangular cross-sectional shape and being flexible for a singular degree of freedom of movement and said preformed, continuously curved section maintaining a curved configuration when in a relaxed state for steering of the guide wire assembly through the vascular system of the body.

* * * * *